US006984753B2

(12) United States Patent
Gnagnetti et al.

(10) Patent No.: US 6,984,753 B2
(45) Date of Patent: Jan. 10, 2006

(54) AGITATION SYSTEM FOR ALKYLBENZENE OXIDATION REACTORS

(75) Inventors: Andreas Gnagnetti, Milan (IT); Luciano Piras, Milan (IT); Kishore K. Kar, Midland, MI (US)

(73) Assignee: Dow Italia s.r.l., Milan (IT)

( * ) Notice: Subject to any disclaimer, the term of this patent is extended or adjusted under 35 U.S.C. 154(b) by 63 days.

(21) Appl. No.: 10/469,678

(22) PCT Filed: Apr. 24, 2002

(86) PCT No.: PCT/US02/13216

§ 371 (c)(1),
(2), (4) Date: Sep. 2, 2003

(87) PCT Pub. No.: WO02/092549

PCT Pub. Date: Nov. 21, 2002

(65) Prior Publication Data

US 2004/0087814 A1    May 6, 2004

Related U.S. Application Data

(60) Provisional application No. 60/291,067, filed on May 15, 2001.

(51) Int. Cl.
*C07C 51/255* (2006.01)
(52) U.S. Cl. .................................................... 562/412
(58) Field of Classification Search ................ 562/412, 562/480; 261/84
See application file for complete search history.

(56) References Cited

U.S. PATENT DOCUMENTS

| | | | |
|---|---|---|---|
| 3,460,810 A | 8/1969 | Mueller et al. | 259/96 |
| 4,231,974 A | 11/1980 | Engelbrecht et al. | 261/87 |
| 4,388,447 A | 6/1983 | Iwamoto et al. | 525/316 |
| 4,699,740 A | 10/1987 | Bollenrath | 261/93 |
| 4,798,131 A | 1/1989 | Ohta et al. | 99/277 |
| 5,102,630 A * | 4/1992 | Lee | 422/224 |
| 5,108,662 A | 4/1992 | Litz et al. | 261/16 |
| 5,536,875 A | 7/1996 | Roby et al. | 562/412 |
| 5,791,780 A | 8/1998 | Bakker | 366/317 |
| 5,972,661 A | 10/1999 | Kubera et al. | 435/104 |

FOREIGN PATENT DOCUMENTS

WO    WO 97/25133    7/1997

OTHER PUBLICATIONS

Database WPI. Section Ch, Week 198516. Derwent Publications Ltd. AN 1985-097623. XP002163361 & SU 1 115 791 (VOLKOV I A) Sep. 30, 1984 abstract; figure 1.
Database WPI. Section Ch, Week 199145. Derwant Pub. Ltd., AN 1991-331560, XP002163361 & SU 1 632 493 A (SHISKIN A V) Mar. 7, 1991 abstract; figure.

* cited by examiner

*Primary Examiner*—Paul A. Zucker

(57) ABSTRACT

A process for producing aromatic dicarboxylic acids by the oxidation of dimethylbenzenes wherein dimethylbenzenes are mixed with an oxygen containing gas, solvent and catalyst in a reactor and the reaction mixture is agitated with one or more asymmetric radial impellers in combination with at least one axial impeller.

11 Claims, 6 Drawing Sheets

AGITATION SYSTEM FOR ALKYLBENZENE OXIDATION REACTORS

This application is filed pursuant to 35 USC 371 based upon PCT/US02/13216, filed Apr. 24, 2002, which claims the benefit of U.S. Application No. 60/291,067, filed May 15, 2001.

This invention relates to an improved agitation system for large scale crude terephthalic acid ("CTA") oxidation reactors which improves gas-liquid mass transfer. The system consists of a gas dispersing radial turbine such as a Bakker Turbine (BT6) in combination with one or more axial impeller(s), such as pitch blade turbine(s), in the down pumping mode. Gas is preferably sparged through the nozzles near the blade tip.

Crude terephthalic acid is obtained by oxidation of the methyl groups of p-xylene. The reaction is performed by sparging air or other oxygen containing gas through an organic mixture (p-xylene and acetic acid) and catalyst, typically together with a recycle stream. Heat generated by the oxidation reaction is removed by the vaporization of solvent and reaction water. The temperature in the reactor is controlled by the vaporization of solvent and reaction water and by the recycle in the reactor of a condensate stream of the overhead vapors. The oxidation reactor is a continuous stirred tank reactor, normally at a temperature of 180 to 205° C. and a pressure of 15 to 18 bar. CTA is recovered from the reactor effluent via crystallization and filtration. It is desired to improve the quality of the CTA in terms of color and impurities, such as 4-carboxy-benzaldehyde.

It is known in the art that mass transfer is an important factor for the overall conversion of p-xylene and CTA quality. It is essential in designing and optimizing the oxidation reactor for enhanced PTA productivity and quality to understand gas-liquid mass transfer, while comparing different agitator configurations. Furthermore, the mass transfer efficiency is even more critical as the current trend in the industry is to reduce capital and operating costs which has led to bigger plants (500 kT/yr or more) with a single oxidation reactor, as opposed to the parallel reactors which were used in former times. The desire to improve gas-liquid mass transfer in the CTA reactors has recently spawned some unique agitation system designs, and the truly optimal design will set the competitive advantage in PTA technology licensing.

BT6 is the product name for the Bakker Turbine designed and marketed by Chemineer Inc. It is a radial gas dispersing impeller that is claimed to be less susceptible to flooding. Like the Rushton and Concave disk impellers, the BT6 consists of six blades extending radially from a disk. These blades are parabolic in shape, like the SRGT (SCABA) blades, but their upper arc is longer than their bottom arc. It has been discovered that this turbine design when used in combination with axial impellers would offer improved mass transfer in the reaction system used to produce aromatic dicarboxylic acids such as terephthalic acid. The use of radial asymmetric blades such as the BT6 together with one or more axial impellers would offer superior gas-liquid mass transfer in CTA reactors.

Accordingly the present invention relates to a process for producing aromatic dicarboxylic acids such as terephthalic acid by the oxidation of dimethylbenzenes such as p-xylene wherein the dimethylbenzenes is mixed with an oxygen containing gas, solvent and catalyst in a reactor, the improvement comprising agitating the reaction mixture with one or more asymmetric radial impellers in combination with at least one axial impeller.

Suitable asymmetric radial impellers are described in U.S. Pat. No. 5,791,780. As disclosed in that reference, in general, the asymmetric radial impeller will include a plurality of generally radially extending blades. Each of the blades will include upper and lower sheet-like portions which meet at a vertex, such that the cross-section of the blade will be generally parabolic or u-shaped. The width of the upper portion of each blade will be longer than the width of the lower portion making the blade asymmetric. Thus, at the leading edge of the blade there will be an upper portion overhang which can capture and disperse rising bubbles. The impeller can have any number of blades, but it is preferred that it has from 4 to 12 blades with 6 being most preferred. The upper sheet should extend 15 to 50 percent further than the width of the lower sheet, with about 25 percent being most preferred. While it is possible to use more than one asymmetric radial impeller in the process of the invention, a single impeller is generally preferred.

Axial impellers are generally known in the art and any such impellers may be used in the present invention. For example, a double helix impeller such as the one depicted in U.S. Pat. No. 5,108,662, or an airfoil blade impeller such as the one depicted in U.S. Pat. No. 4,231,974 could be used in this invention. Other suitable axial impellers include Pitch Blade Turbine, high efficiency impellers (such as model A-310 from Lightnin Mixing Co, HE-3 from Chemineer, Inc. and Viscoprop from EKATO Rueher and Mischtechnik GmbH), single helixes or marine props (such as A-315 or A-320 from Lightnin Mixing Co., MT-4, or MY-4 from Chemineer, Inc.). The number of axial impellers used in general depends on the viscosity of the working media. The more viscous the working media the more axial impellers are warranted. It is contemplated that the invention may comprise from 1 to several axial impellers 2, but it is preferred that there be two.

The present invention may also include the use of a draft tube. Draft tubes and their modifications are known in the art, and those teachings are generally applicable to this invention. For example, the draft tube can be slotted to provide for return of liquid to the center of the draft tube if the level of liquid for some reason does not exceed the top of the draft tube. Also, the use of vertical baffles on the inner surface of the draft tube can be advantageously used to redirect tangential flow to axial flow. If baffles are used in the draft tube it is preferred that they have a width of 0.8 to 0.1 of the draft tube inner diameter with a clearance of 0.016 to 0.021 of the draft tube inner diameter. Moreover, the use of a baffle to partially close of the bottom of the cylinder formed by the draft tube is shown, inter alia, in U.S. Pat. No. 5,536,875 and may also be used in the present invention.

Although the dimensions of the draft tube are not critical to the present invention, it has been found that the optimum radius of the draft tube is 0.707 of the tank radius. Using a draft tube of this radius make the cross sectional area of the tank which is inside the draft tube equal the cross sectional area of the tank which is outside the draft tube. The draft tube can optionally contain a conically flared portion, at the entrance end of the draft tube. It is believed that this section will aid in straightening the flow of the reactor contents. The angle of the bevel should be between 30 and 60 degrees, with 45 degrees being most preferred. The beveled edge should not be too long, such that it restricts flow around the top of the draft tube. It is preferred if the length of the beveled edge is from zero to about one fourth of the draft tube's inner diameter, with about $1/12$ of the length being most preferred.

EXAMPLES

In order to demonstrate the surprising effectiveness of the present invention, a series of gas-liquid experiments were carried out to study the flow and mass transfer performance of the asymmetrical radial impellers such as the Bakker turbine (BT6) impeller. The experimental k-factor, gas-hold-up, and the mass transfer coefficient ($k_L a$) values of the BT6 agitator were compared with those of Rushton turbine. All the tests were conducted in an air-water or an air-water-acetic acid system. Since the working media is different from that in the CTA reactor, the results characterize the relative performance of the gas dispersing impellers in combination with an axial impeller such as the pitched blade turbine (PBT). Under reaction temperature and pressure conditions in the CTA reactor, absolute volumetric mass transfer coefficient ($k_L a$) values could be significantly different from those in the present experimental air-water system.

There are two general techniques, that is, the transient and steady-state methods, for evaluation of the combined liquid film mass transfer coefficient and interfacial area ($k_L a$). In this experiment, the steady-state method was used. The concentration of oxygen in the liquid is monitored by a dissolved oxygen (D.O.) probe. When steady state is reached, that is, the oxygen concentration remains constant, the D.O. value is recorded. The value of $k_L a$ is determined from the oxygen transfer rate and the oxygen concentration in the liquid. Due to the presence of salt and $H_2O_2$ in water, the $k_L a$ values calculated with this method are usually higher than those obtained with the transient method.

Figure 1:
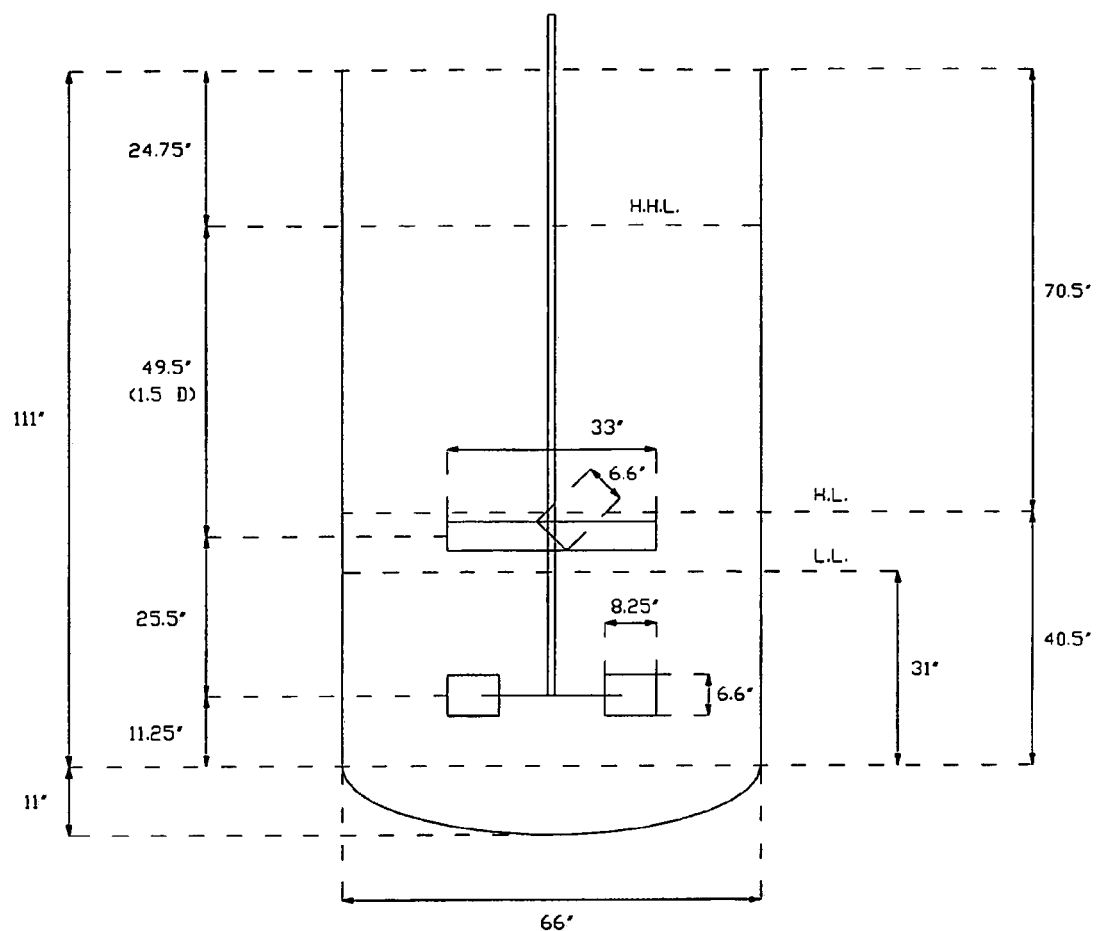
FIG. 1 shows the tank geometry and agitation system design for the tank used in the examples.

All the experiments were carried out in an ASME dish bottom 66" (1676 mm) diameter, 1800 gal (6.814 m³) tank. The tank had four flat baffles and four side entry ¾" ID tangential air nozzles. The nozzles are positioned near the impeller tips. The tank geometry and agitation system designs are summarized in FIG. 1 and Table I.

TABLE 1

Summary of the tank geometry and agitation system designs

| Vessel Volume Data | Radial Impeller Data (D = impeller diameter) |
|---|---|
| Bottom head: 100.67 gal (0.381 m³)<br>Vessel total: 1744.62 gal (6.60 m³) | Blade length: L = 0.25 D<br>Blade width: W = 0.20 D<br>Disk diameter: d = 0.67 D |

The dissolved oxygen concentration was measured using a D.O. probe. The probe was mounted on a rod and positioned at each of three different heights, while pointing against the direction of tangential flow. The three different heights were 16.5" above the upper impeller axis, 13" below the upper impeller axis (between the two impellers), and 11" below the bottom impeller (below the air sparger, as well). These probe positions were reproducible due to an interlocking nut affixed to the rod.

Hydrogen peroxide solution, at 35 wt. percent., was metered into the tank. Conductivity was measured before and after the tests using a conductivity meter. Temperatures in the head space and the liquid were measured. The flow rate of air was controlled by a data acquisition and control system. Agitator rpm and shaft power were also measured.

Figure 2:
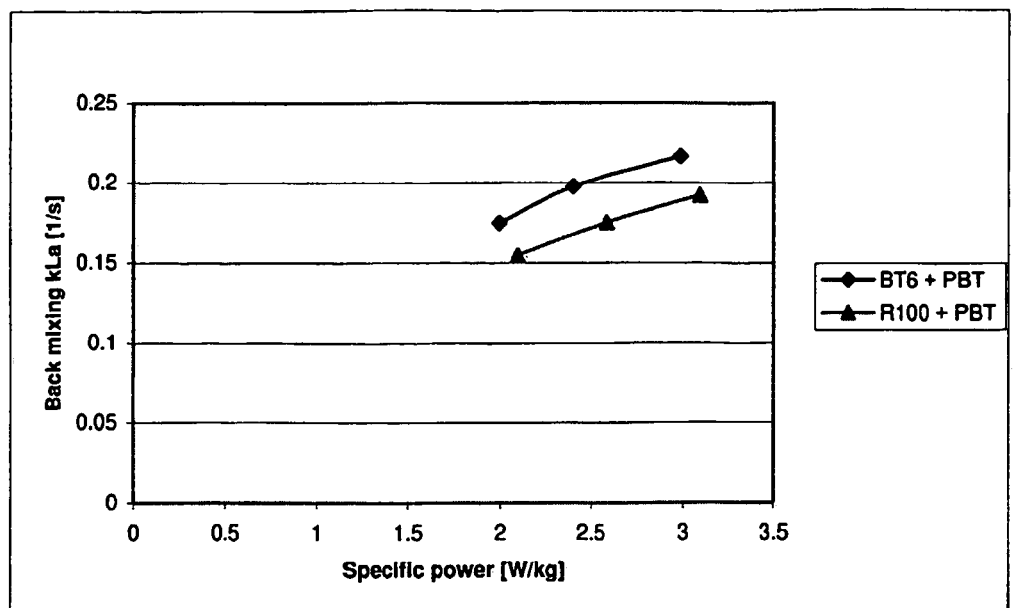
FIG. 2 shows back mixing $k_L a$ [1/s] versus power per mass [W/kg] with the dissolved oxygen probe in the bottom position at 20° C. (gas velocity 0.043 m/s at 1.4 VVM).
Figure 3:
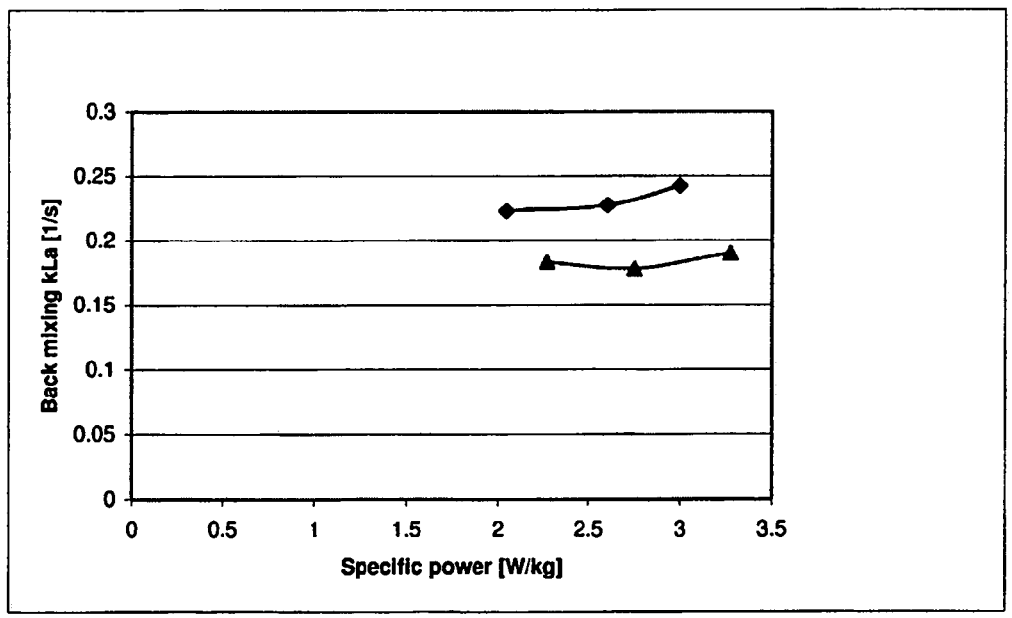
FIG. 3 shows back mixing $k_L a$ [1/s] versus power per mass [W/kg] with the dissolved oxygen probe in the middle position at 20° C. (gas velocity 0.043 m/s at 1. VVM).
Figure 4:
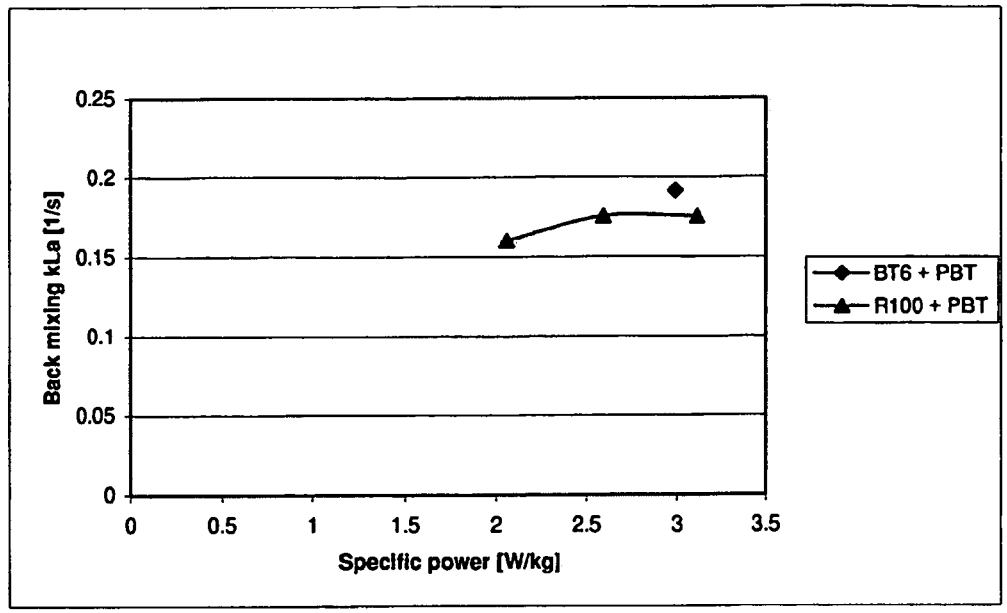
FIG. 4. shows back mxing $k_L a$ [1/s] versus power per mass [W/kg] with the dissolved oxygen probe in the top position at 20° C. (gas velocity 0.043 m/s at 1.4 VVM).

FIGS. 2 to 4 show the volumetric mass transfer coefficients at different locations in the tank, as a function of specific power at 1.4 VVM (superficial gas velocity=0.043 m/s). The agitation systems used in obtaining this data included the PBT and either the Bakker (BT6) or Rushton turbine. Table 2 shows the relative mass transfer performance of the BT6 turbine as compared to the Rushton turbine.

FIGS. 2 to 4 clearly show that the mass transfer performance of BT6+PBT was surprisingly superior (~17%) to Rushton+PBT. The average volumetric mass transfer coefficients in these systems were found to be 0.210 and 0.176 sec⁻¹ for the BT6 and Rushton turbines, at 20° C., respectively. It is believed that the asymmetric parabolic profiles of the BT6 blades help restore gas bubbles in the bottom head, thus enhancing the mass transfer coefficient in this region of the tank. Since CTA reactors are typically quite large, the volume of their bottom semi-elliptical head can be on the order of ca. 60 m³ in a 500 kT/yr PTA production plant. Therefore, mass transfer improvement in the bottom head region is critical.

TABLE 2

Mass transfer performance of the BT6 + PBT agitation systems, relative to the Rushton + PBT system, at the various sample positions in the tank

|  | BT6 + PBT |
|---|---|
| Top | +9.23% |
| Middle | +27.76% |
| Bottom | +12.58% |
| OVERALL | +16.52% |

Figure 5:
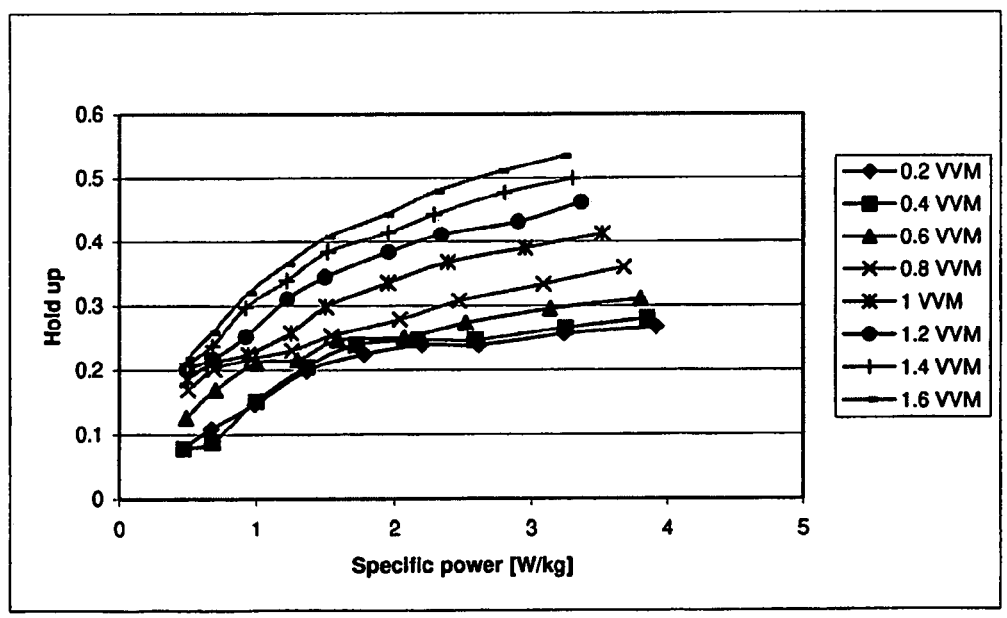
FIG. 5 shows gas hold-up versus power per mass [W/kg] for the BT6+PBT system at different air flow rates for an aerated acetic acid solution.
Figure 6:
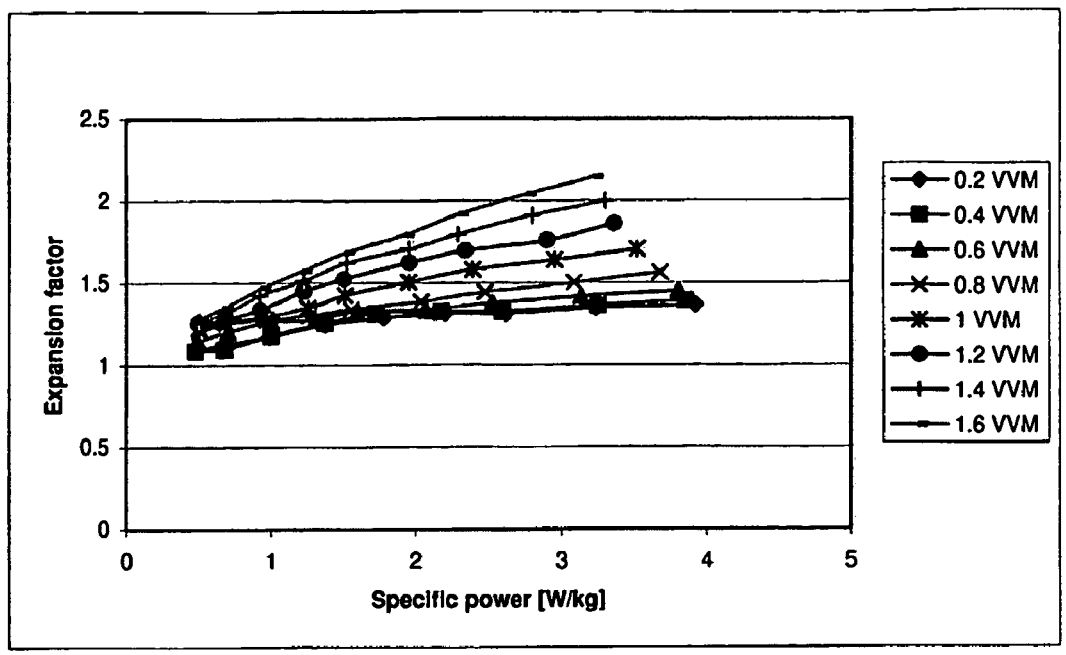
FIG. 6 shows the expansion factor versus power per mass [W/kg] for the BT6+PBT system at different air flow rates for an aerated acetic acid solution.

Tests were also performed using acetic acid solution to determine the gas hold-up and the expansion factor. The acetic acid solution was tailored to simulate the physical conditions of the CTA reactor working media. FIGS. 5 and 6 show the gas hold-up and expansion factor versus specific power consumption for different gas flow rates. The results shown in these figures were in good agreement with real industrial reactors where the expansion factor is about 2.

Figure 7:
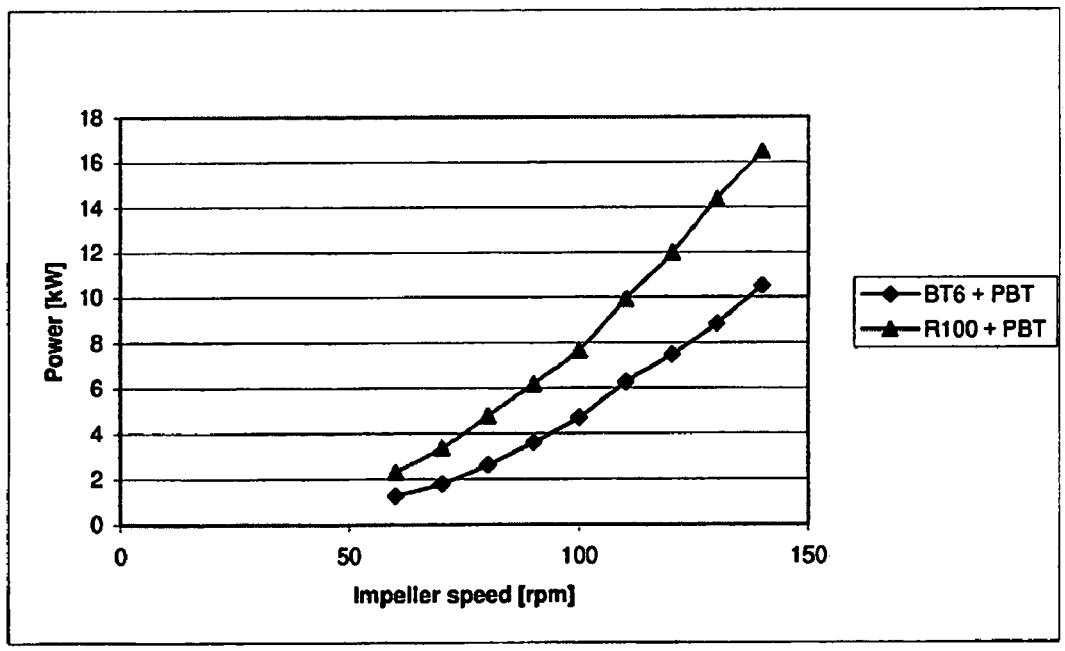
FIG. 7 shows the comparison of ungassed power consumption [kW] versus impeller speed [rpm] for two different agitation systems at 0 VVM.

To obtain the power draw characteristics of different agitation systems, tests were carried out in unaerated and aerated acetic acid solution media. FIG. 7 shows the power draw for different agitation systems as a function of impeller speed under ungassed condition.

Figure 8:
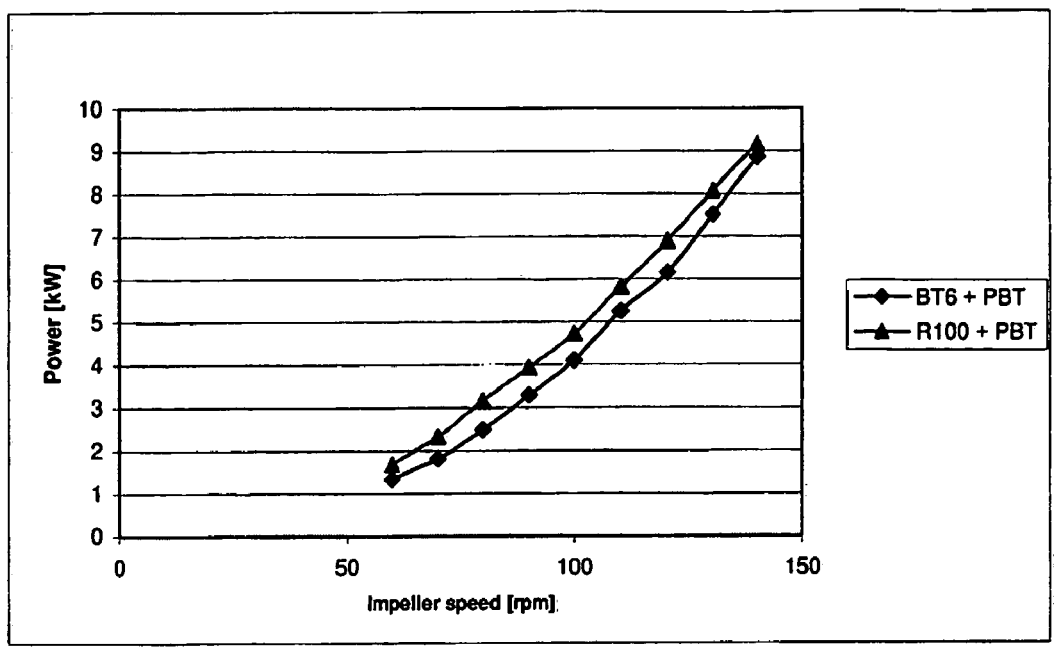
FIG. 8 shows the comparison of power consumption [kW] versus impeller speed [rpm] of two agitation systems at 1.4 VVM

Observations similar to those from FIG. 7 can be seen from the results shown in FIG. 8, which represents gassed conditions at 1.4 VVM. As expected, the power draws differ due to differences in the shape of these radial impeller blades. The agitation system containing the BT6 consistently drew the least power at all conditions considered. In a typical 500 kT/yr PTA plant, the CTA reactor uses a ca. 1000 kW drive system and operates at dual speeds to accommodate the power draw during either gassed or ungassed conditions. Thus, a clear understanding of the gassed and ungassed power draw is vital to the cost-effective design of the CTA reactor.

Figure 9:
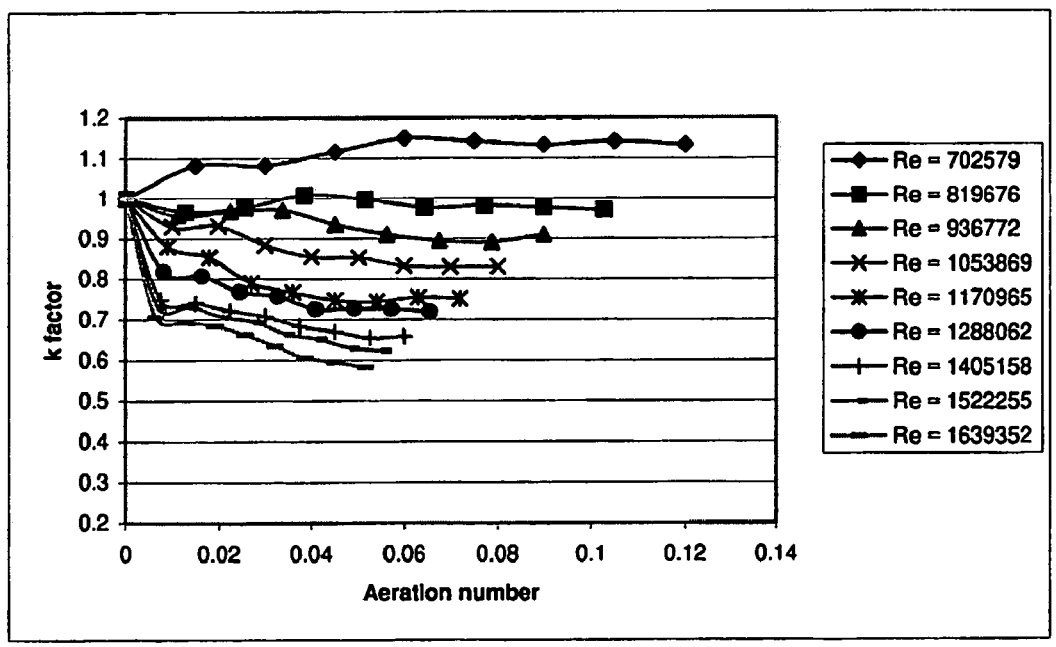
FIG. 9 shows the power draw (k-factor versus aeration number) for the BT6+PBT system.
Figure 10:
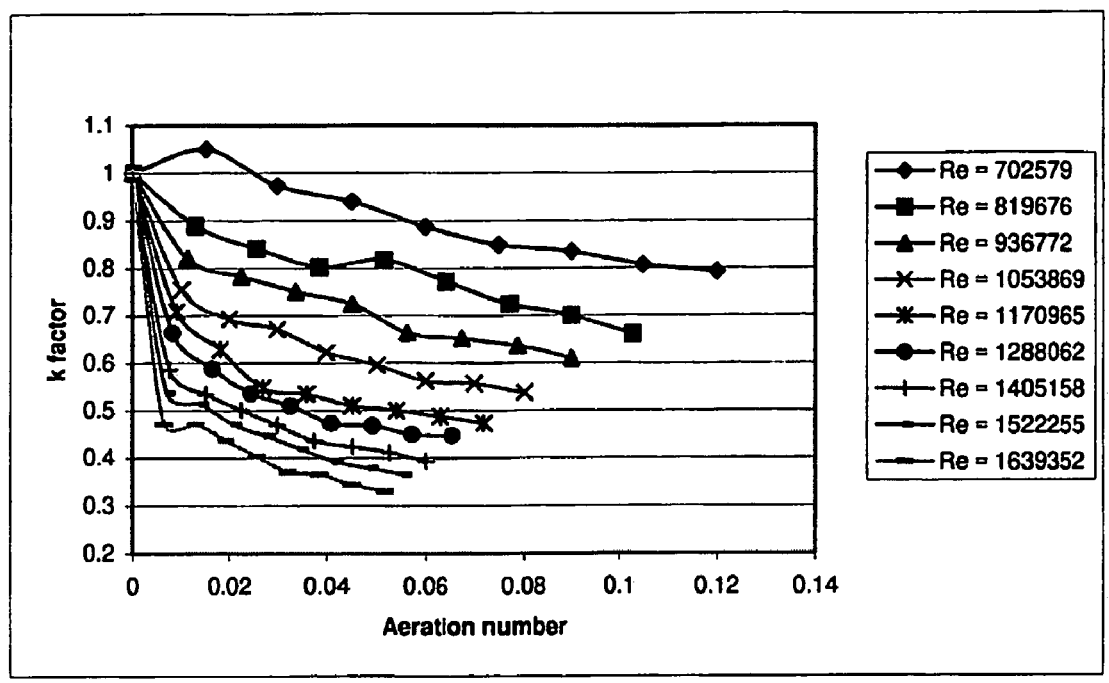
FIG. 10 shows the power draw (k-factor versus aeration number) for the Rushton+PBT system.

The ratio of gassed power to ungassed power, known as the k-factor, is used in determining drive system requirements. FIGS. 9 and 10 present k-factors versus aeration numbers for two agitation systems at various gassing conditions (0.0 to 1.6 VVM by steps of 0.2) and agitation rates (60 to 140 RPM). The figures' curves include nine aeration numbers at various fixed values of impeller Reynolds number (Re).

Each curve in FIGS. 9 and 10 reaches an operating region where increased aeration number doesn't change the k-factor dramatically. While none of the curves show the k-factor suddenly increasing with aeration number, an indication that the impeller system has started to flood, it should be remembered that this data is also influenced by the PBT coupled to each radial impeller (BT6 or Rushton).

Initiation of gas flow caused k-factors in FIGS. 9 and 10 to decrease most dramatically (30 to 50%) for the Rushton-based agitator system. More significantly, k-factors for the BT6-based system never dropped below 0.6, while those for Rushton-based systems dropped as low as 0.35.

Table 3 contains data from the figures, and represents the highest fixed values of impeller Reynolds number (at a 140 RPM agitation rate) and aeration number (at 1.6 VVM). The table data show a significant advantage in the power requirements of the BT6 (10.5 kW/14 Hp), as compared to the Rushton impeller system (>16.5 kW/>22 Hp). This effect is due to vortex shedding and pressure drop in the wake region (behind the impeller blades), which increases in the order: BT6<Rushton.

TABLE 3

Power requirements and k-factors for the BT6 + PBT and Rushton + PBT agitation systems, at fixed operating conditions (acetic acid coalescing media)

| | BT6 + PBT | Rushton + PBT |
|---|---|---|
| Agitation rate (RPM) | 140 | 140 |
| Reynolds number | $1.64 \times 10^6$ | $1.64 \times 10^6$ |
| Aeration number | 0.10 | 0.10 |
| k-factor | 0.6 | <0.35 |
| Ungassed Power (kW/Hp) | 10.5/14 | >16.5/>22 |

The lower power requirements of the BT6-based system means lower operating costs, while also adding the ability to operate at a higher agitation rates than with the other impeller systems. Additionally, k-factors with a value nearer to 1.0 make the BT6 better able to operate at the same speed whether operating under gassed or ungassed conditions. This provides another very significant savings, in the initial capital cost of the impeller drive system, because only a single speed drive is required.

These experiments showed that the most effective gas-liquid-solid mixing technology for the stirred tank reactors used in CTA oxidation includes:
(1) the BT6 impeller in combination with one or more axial impeller(s), such as pitch blade turbine(s), in the down pumping mode
(2) gas sparged through tangential nozzles that are positioned near the impeller tips, but just below the horizontal centerline of the blades Advantages of the BT6 agitation system over either concave disks or Rushton turbines are superior mass transfer performance, lower ungassed power consumption, less susceptibility to flooding at high aeration rates, and better solids suspension. Lower ungassed power requirements of the BT6 will significantly reduce capital costs of the agitator drive system, by needing only one speed instead of two.

The reduction in acetic acid consumption is estimated as ca. 10 percent and the increase of yield of p-xylene is estimated as ca. 0.5 to 1 percent.

What is claimed is:

1. In a process for producing aromatic dicarboxylic acids by the oxidation of dimethylbenzenes wherein the dimethylbenzenes are mixed with air, solvent and catalyst in a reactor, comprising agitating the reaction mixture with one or more asymmetric radial impellers in combination with at least one axial impeller.

2. The process of claim 1 wherein the aromatic dicarboxylic acid is terephthalic acid and the methylbenzene is p-xylene.

3. The process of claim 1 wherein the aromatic dicarboxylic acid is isophthalic acid and the methylbenzene is m-xylene.

4. The process of claim 1 wherein the aromatic dicarboxylic acid is ortophthalic acid and the methylbenzene is o-xylene.

5. The process of claim 1 wherein a draft tube is used to further improve the gas-liquid mass transfer.

6. The process of claim 1 wherein the radial impeller comprises multiple parabolic shaped blades extending radially from a disk with each blade having an upper arc longer than its bottom arc.

7. The process of claim 1 wherein the axial impeller is a pitched blade turbine impeller.

8. The process of claim 1 wherein the oxygen-containing gas is sparged into the reactor through tangential nozzles that are positioned near the asymmetric radial impeller tips, and slightly below a horizontal centerline of the asymmetric radial impeller.

9. A process for producing aromatic dicarboxylic acids by oxidation of dimethylbenzenes comprising: agitating dimethylbenzenes with air, solvent and catalyst in a reactor with an agitation system comprising a combination of at least one asymmetric radial impeller with at least one axial impeller selected from a: pitched blade, airfoil blade, high efficiency, and marine.

10. A process for producing aromatic dicarboxylic acids by oxidation of dimethylbenzenes comprising: agitating dimethylbenzenes with an oxygen containing gas, solvent and catalyst in a reactor with an agitation system comprising a combination of at least one asymmetric radial impeller with at least one pitched blade impeller.

11. The process of claim 10 where in the oxygen containing gas comprises air.

\* \* \* \* \*